(12) United States Patent
Mahoney et al.

(10) Patent No.: US 7,892,260 B2
(45) Date of Patent: Feb. 22, 2011

(54) UNILATERAL PLACEMENT

(75) Inventors: Michael Mahoney, Middletown, RI (US); Christopher Ramsay, New Bedford, MA (US); John Riley Hawkins, Cumberland, RI (US); Erin Dupak, Fall River, MA (US); Jayson Varghese, Dorchester, MA (US); Charles M. Bartish, Jr., Providence, RI (US); Jonathan Fanger, Fall River, MA (US); SeungKyu Daniel Kwak, Grafton, MA (US)

(73) Assignee: DePuy Spine, Inc., Raynham, MA (US)

( * ) Notice: Subject to any disclaimer, the term of this patent is extended or adjusted under 35 U.S.C. 154(b) by 552 days.

(21) Appl. No.: 11/539,295

(22) Filed: Oct. 6, 2006

(65) Prior Publication Data

US 2008/0161858 A1 Jul. 3, 2008

(51) Int. Cl.
*A61B 17/70* (2006.01)
(52) U.S. Cl. .................. 606/265; 606/305; 606/308
(58) Field of Classification Search ......... 606/246–250, 606/264–278, 300–321
See application file for complete search history.

(56) References Cited

U.S. PATENT DOCUMENTS

| 5,133,717 A * | 7/1992 | Chopin .................. 606/301 |
| 5,147,360 A * | 9/1992 | Dubousset .............. 606/250 |
| 7,645,294 B2 * | 1/2010 | Kalfas et al. ............ 606/250 |
| 2001/0020169 A1 | 9/2001 | Metz-Stavenhagen |
| 2003/0114853 A1 | 6/2003 | Burgess et al. |
| 2004/0162558 A1 | 8/2004 | Hegde et al. |
| 2005/0228387 A1 | 10/2005 | Paul |
| 2005/0277929 A1 | 12/2005 | Raiszadeh |
| 2005/0283153 A1 | 12/2005 | Poyner et al. |
| 2006/0025768 A1 | 2/2006 | Iott et al. |
| 2008/0086130 A1 | 4/2008 | Lake et al. |

FOREIGN PATENT DOCUMENTS

DE 29818831 U1 12/1998

(Continued)

OTHER PUBLICATIONS

Suk, et al., "Unilateral *Versus* Bilateral Pedicle Screw Fixation in Lumbar Spinal Fusion", Spine, vol. 25, No. 14, pp. 1843-1847, 2000.

(Continued)

*Primary Examiner*—Todd E Manahan
*Assistant Examiner*—Christina Negrelli
(74) *Attorney, Agent, or Firm*—Nutter McClennen & Fish LLP

(57) ABSTRACT

Methods and devices are provided for spinal fixation. In one exemplary embodiment, the methods and devices provide one or more points of fixation located adjacent to a first fixation point at which a bone anchor is implanted in bone. For example, an extension member can be coupled, either directly or indirectly, to a bone anchor, and a fastener can be used to anchor the extension member to bone at a second point of fixation adjacent to the first point of fixation. The second point of fixation can be effective to prevent rotation or other movement of the bone anchor, thereby stabilizing the bone anchor. The methods and devices are particularly useful for unilateral fixation, in which one or more levels of the spine are stabilized along a single lateral side of the spine.

14 Claims, 5 Drawing Sheets

FOREIGN PATENT DOCUMENTS

| | | |
|---|---|---|
| EP | 0443894 A1 | 8/1991 |
| FR | 2794962 A1 | 12/2000 |
| WO | 0209605 A2 | 2/2002 |

OTHER PUBLICATIONS

Chen, et al., "Biomechanical Analysis of Unilateral Fixation With Interbody Cages", Spine, vol. 30, No. 4, pp. E92-E96, 2005.

Harris, et al., "Transforaminal Lumbar Interbody Fusion", Spine, vol. 29, No. 4, pp. E65-E70, 2004.

Supplementary European Search Report for PCT/US2007019999 dated Nov. 27, 2009.

International Search Report and Written Opinion for PCT/US2007/019999 dated Mar. 28, 2008.

Examination Report for European Patent Application No. 07838235.5 dated Mar. 3, 2010.

\* cited by examiner

UNILATERAL PLACEMENT

FIELD OF THE INVENTION

The present invention relates generally to methods and devices for spinal fixation.

BACKGROUND OF THE INVENTION

Spinal deformities, which include rotation, angulation, and/or curvature of the spine, can result from various disorders, including, for example, scoliosis (abnormal curvature in the coronal plane of the spine), kyphosis (backward curvature of the spine), and spondylolisthesis (forward displacement of a lumbar vertebra). Other causes of an abnormally shaped spine include trauma and spinal degeneration with advancing age. Early techniques for correcting such deformities utilized external devices that applied force to the spine in an attempt to reposition the vertebrae. These devices, however, resulted in severe restriction and in some cases immobility of the patient. Furthermore, current external braces have limited ability to correct the deformed spine and typically only prevent progression of the deformity. Thus, to avoid this need, doctors developed several internal fixation techniques to span across multiple vertebrae and force the spine into a desired orientation.

To fix the spine, surgeons attach one or more spinal connectors (typically rods or plates) to the spine at several fixation sites to correct and stabilize the spinal deformity, prevent reoccurrence of the spinal deformity, and stabilize weakness in trunks that results from degenerative discs and joint disease, deficient posterior elements, spinal fracture, and other debilitating problems. Bone screws are typically used to anchor the spinal connectors at the various fixation sites. Once anchored, the system is under stress and subjected to significant forces, known as cantilever pullout forces. As a result, surgeons are always concerned about the possibility of the implant loosening or the bone screws pulling out of the bone. Thus, surgeons generally seek to attach implants in the most secure and stable fashion possible while at the same time addressing a patient's specific anatomy.

Most current fixation procedures utilize two spinal connectors anchored along opposed lateral sides of the spinal column. Fixation at a single level of the spine typically requires four bone screws. As a result, two incisions are often made in each lateral side of the spine at each fixation level to provide access for inserting the bone screws. In order to avoid the need to create multiple incisions and to reduce the operative and post-operative recovery time, recent fixation trends have utilized unilateral fixation, where only one spinal connector is anchored at various fixation sites along one lateral side of the spine. Because the natural forces through the spine are centered down the middle of the spine, unilateral fixation constructs must be designed to counteract the offset forces. The excess stress applied to current unilateral constructs tend to weaken the bone screws, causing them to rotate within the pedicle, and can weaken the strength of the spinal connector itself.

Accordingly, there is a need in this art for improved methods and devices for unilateral fixation.

SUMMARY OF THE INVENTION

The present invention generally provides methods and device for unilateral fixation. In one embodiment, a unilateral fixation device is provided and includes a bone anchor having a head with a receiving recess formed therein and configured to seat a spinal connector, and a bone-engaging member extending distally from the head and configured to engage bone. The device also includes an extension member extending outward from at least one of the head and the bone-engaging member of the bone anchor. The extension member can include at least one thru-bore formed therein and configured to receive a fastener for anchoring the extension member to bone at a location adjacent to the bone anchor.

The extension member can have a variety of configurations, and it can be removably mated to the head and/or bone-engaging member, or it can be fixedly mated to the head and/or bone-engaging member. In one embodiment, the extension member can include a central opening formed therein for receiving the bone-engaging member of the bone anchor, and the thru-bore(s) can be positioned adjacent to the central opening. For example, the extension member can be in the form of a plate having a plurality of thru-bores formed therein. At least one of the thru-bores can be configured to receive the bone-engaging member of the bone anchor. In one exemplary embodiment, the plate can be substantially circular and it can have a diameter that is larger than a maximum diameter of the head of the bone anchor. In another embodiment, the head of the bone anchor can include opposed arms defining a receiving recess therebetween for seating a spinal connector, and the extension member can be coupled to and extend from one of the opposed arms. The extension member can be, for example, an elongate arm having a thru-bore formed in a terminal portion thereof.

In another embodiment, a unilateral fixation system is provided and includes a bone screw having a head and a shank extending distally from the head and configured to engage bone, a spinal connector configured to be received within the head, and at least one extension member extending laterally from at least one of the head of the bone screw, the shank of the bone screw, and the spinal connector. The extension member(s) can include at least one thru-bore formed therein for receiving a fastener for anchoring the extension member to bone such that the extension member prevents rotation of the bone screw relative to bone. The extension member(s) can be removably mated to at least one of the head of the bone screw, the shank of the bone screw, and the spinal connector, or it can be fixedly mated to at least one of the head of the bone screw, the shank of the bone screw, and the spinal connector.

While the extension member(s) can have a variety of configurations, in one embodiment the extension member(s) can extend laterally from a terminal portion of the spinal connector. For example, a first extension member can extend laterally from a first terminal portion of the spinal connector, and a second extension member can extend laterally from a second terminal portion of the spinal connector. In another embodiment, the extension member can include a cross-connector removably matable to the spinal connector, and an arm movably coupled to the cross-connector and having a thru-bore formed in a terminal portion thereof for receiving a fastener for anchoring the extension member to bone.

Methods for spinal fixation are also provided and in one embodiment the method can include implanting a bone anchor at a first fixation point in a lateral side of a vertebra of a spine, coupling a spinal connector to the bone anchor such that the spinal connector extends along the lateral side of the spine, and implanting a fastener in the vertebra adjacent to the bone anchor. The fastener can extend through an extension member extending from the bone anchor such that the fastener provides a second point of fixation adjacent to the first point of fixation. The second point of fixation can be at various locations, and in one embodiment the second point of fixation can be in the spinous process of the vertebra. The method can also include implanting a plurality of bone anchors in a lateral side of a plurality of adjacent vertebrae, and mating the spinal connector to the plurality of bone anchors to unilaterally affix the adjacent vertebrae to one another.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
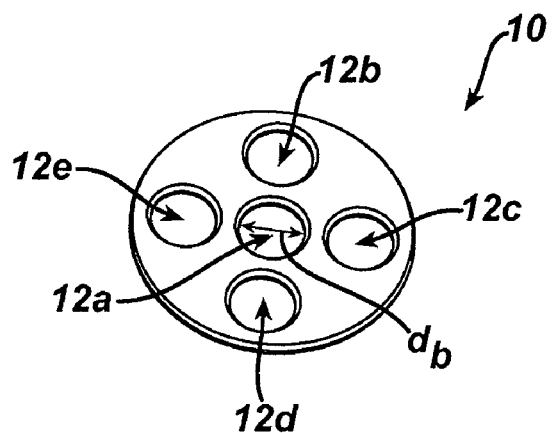
FIG. 1A is a perspective view of one embodiment of an extension member in the form of a plate adapted to mate to a bone screw, and having a plurality of thru-bores formed therein for receiving one or more fasteners for anchoring the extension member to bone to prevent rotation of the bone screw.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for spinal fixation. In one exemplary embodiment, the methods and devices provide one or more points of fixation located adjacent to a first fixation point at which a bone anchor is implanted in bone. For example, an extension member can be coupled, either directly or indirectly, to a bone anchor, and a fastener can be used to anchor the extension member to bone at a second point of fixation adjacent to the first point of fixation. The second point of fixation can be effective to prevent rotation or other movement of the bone anchor, thereby stabilizing the bone anchor. The methods and devices are particularly useful for unilateral fixation, in which one or more levels of the spine are stabilized along a single lateral side of the spine. A second point of fixation is particularly desirable with unilateral fixation, as the natural forces through the spine are centered down the middle of the spine and thus the second point of fixation helps to counteract the offset forces applied to the bone anchors.

A person skilled in the art will appreciate that, while the methods and devices are particularly useful for unilateral fixation, the methods and devices can be used in various procedures in which it is desirable to provide a more secure connection between a bone anchor, an implant, or other spinal devices and bone. A person skilled in the art will also appreciate that the term unilateral fixation is intended to include both rigid fixation in which movement between adjacent vertebrae is prevented, and dynamic fixation in which adjacent vertebrae are stabilized relative to one another but a limited amount of motion is allowed between the adjacent vertebrae. With rigid fixation, for example, one or more bone anchors can be coupled to one another by a rigid spinal connector, such as a spinal rod. With dynamic fixation, for example, one or more bone anchors can be coupled to one another by a dynamic spinal connector, such as a flexible spinal rod, a dynamic or flexible spinal plate, or other devices that will allow motion between the adjacent vertebrae. Commonly-owned U.S. Publication No. US-2008-0086130, filed on even date herewith and entitled "Torsionally Stable Fixation," by Lake et al., which is hereby incorporated by reference in its entirety, discloses various exemplary spinal connectors that can be used with the spinal anchors disclosed herein. The spinal connectors are particularly configured for use during unilateral fixation, and thus can further provide a more secure spinal fixation construct.

FIG. 1A illustrates one exemplary embodiment of an extension member 10 that is adapted to couple to a bone anchor implanted at a first fixation point, and that is adapted to receive a fastener for affixing the extension member to bone at a second fixation point adjacent to the first fixation point. As shown, the extension member is in the form of a generally planar plate 10 having a circular shape. The plate 10 can, however, have virtually any shape and size depending on the type of fastener intended to be used with the plate 10. As further shown, the plate 10 can include several thru-bores 12a, 12b, 12c, 12d, 12e formed therein. One of the thru-bores, e.g., thru-bore 12a, can be configured to receive a bone anchor therethrough, and one or more additional thru-bores, e.g., thru-bores 12b-d, can be configured to receive a fastener therethrough for providing a second point of fixation. In the illustrated embodiment, the plate 10 is shown having a central opening thru-bore 12a that is configured to receive a bone anchor, such as a bone screw, and four additional thru-bores 12b-d surround the central thru-bore 12a for receiving a fastener, such as a wire, screw, nail, etc. The thru-bores can have the same shape and size, or they can differ from one another.

Figure 1B:
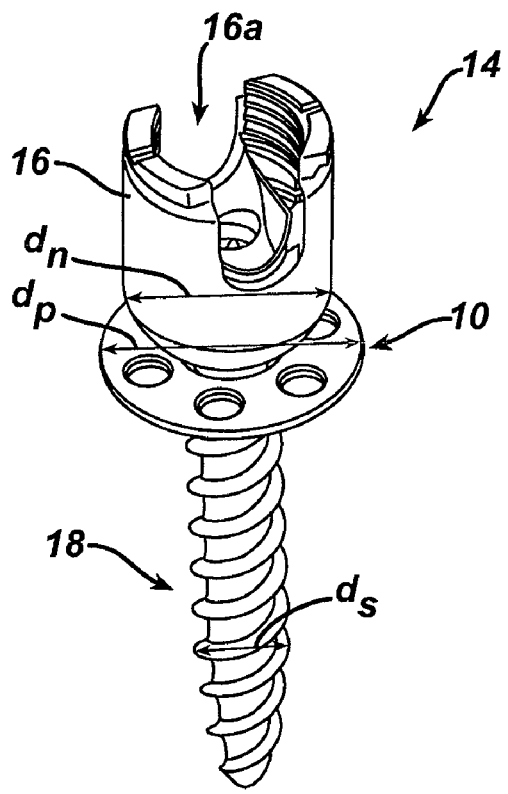
FIG. 1B is a perspective view of a bone screw coupled to the extension member of FIG. 1A.

FIG. 1B illustrates the plate 10 in use with a bone anchor. In this embodiment, the bone anchor is in the form of a bone screw 14, however various other bone anchors, such as spinal hooks, plates, etc., can be used. The bone screw 14 generally includes a head 16 having a U-shaped recess 16a formed therein for seating a spinal connector, such as a spinal rod or plate, and a threaded shank 18 extending distally from the head 16. The shank 18 is disposed through the central thru-bore 12a in the plate 10. In order to prevent the head 16 from passing through the central thru-bore 12a, the central thru-bore 12a can have a diameter $d_b$ (FIG. 1A) that is larger than a diameter $d_s$ of the shank 18, but that is smaller than a diameter $d_h$ of the head 16. The plate 10 can also have a diameter $d_p$ that is larger than the maximum diameter $d_h$ of the head 16 of the bone screw 14 to expose the thru-bores 12b-e that surround the central thru-bore 12a. This will allow a fastener, such as a nail, spike, tack, staple, wire, rivet, hook, clamp, expandable fastener, bolt, screw, etc., to be inserted through one or more of the thru-bores 12b-e in the plate 10. The fastener will thus provide one or more additional points of fixation that are adjacent to the first point of fixation, i.e., the implant site of the bone screw 14. As a result, the plate 10 will prevent undesired movement of the shank 18 of the bone screw 14 thereby preventing loosening of the bone screw 14. As previously explained, this is particularly advantageous during unilateral fixation to counteract the offset forces applied to the bone screw 14.

A person skilled in the art will appreciate that the plate 10 can have a variety of other configurations. For example, the central thru-bore 12a in the plate 10 can have a shape that is configured to engage the shank 18 and/or head 16 of the bone screw 14 to prevent rotation between the plate 10 and the bone screw 14. Such a configuration will thus prevent rotation of the bone screw 14 once implanted, as the second point of fixation will prevent rotation of the plate 10 which is non-rotatably mated to the bone screw 14. In other embodiments, the plate 10 can be fixedly mated to or formed integrally with the bone screw 14 or other bone anchor to prevent rotation and other movement of the bone screw 14 once implanted.

Figure 2A:
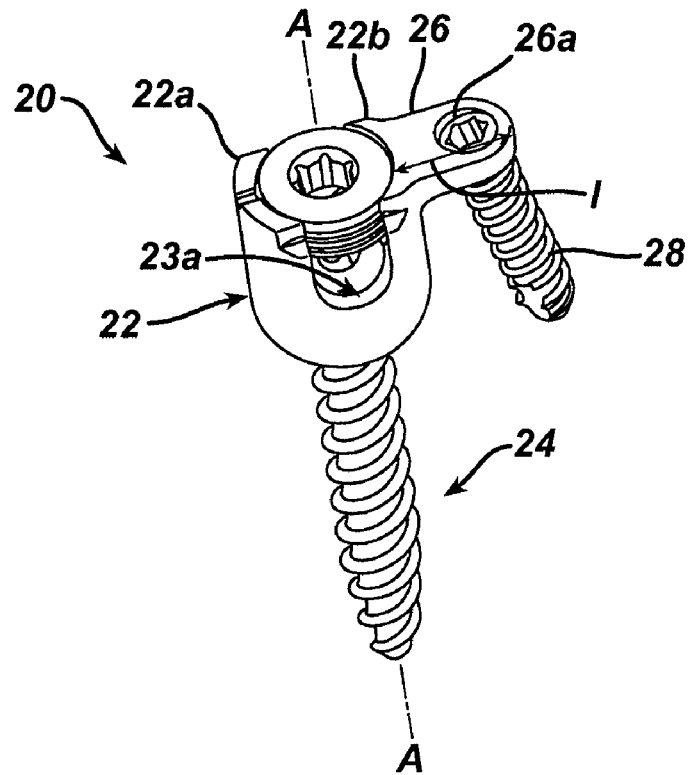
FIG. 2A is a perspective view of another embodiment of an extension member in the form of an extension arm extending laterally from a head of a bone screw and having a secondary bone screw extending therethrough for anchoring the extension member to bone to prevent rotation of the bone screw.
Figure 2B:
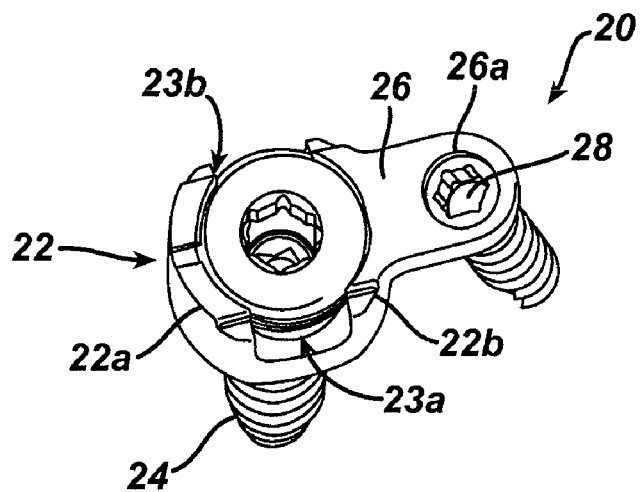
FIG. 2B is a top view of the bone screw and extension member of FIG. 2A.

FIGS. 2A-2B illustrate another embodiment of an extension member for providing an additional point of fixation. In this embodiment, the extension member is in the form of an extension arm 26 that is fixedly mated to or integrally formed with the head 22 of a bone screw 20. In particular, the extension arm 26 is shown mated to and extending laterally outward from a head 22 of a bone screw 20. The bone screw 20 is similar to the bone screw 14 shown in FIG. 1B, and generally includes a U-shaped head 22 having opposed arms 22a, 22b that define opposed U-shaped receiving recesses 23a, 23b therebetween, and a threaded shank 24 that extends distally from the U-shaped head 22. The extension arm 26 is mated to or formed on a proximal or terminal end of one of the opposed arms, e.g., arm 22b, of the head 22, and it extends in a direction that is generally perpendicular to a longitudinal axis A of the bone screw 20. The extension arm 26 can, however, extend at other angles relative to the axis A of the bone screw 20, and the angle can be adjusted depending on the desired anchor site of the extension arm 26.

Figure 3:
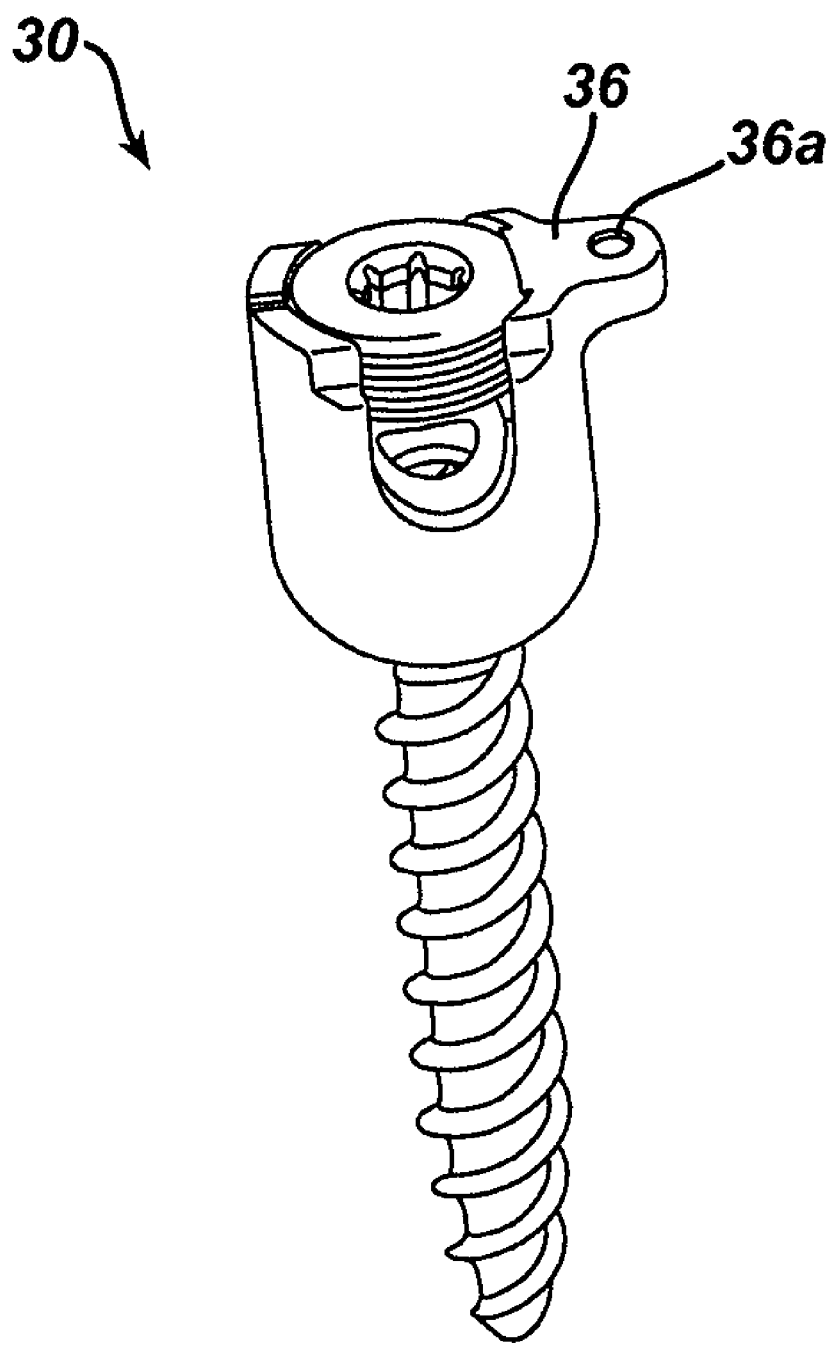
FIG. 3 is a perspective view of another embodiment of an extension member in the form of an extension arm extending laterally from a head of a bone screw and having a thru-bore configured to receive a wire for anchoring the extension member to bone to prevent rotation of the bone screw.

The particular configuration of the extension arm 26 can vary, and it can have a generally planar configuration as shown, or it can have a shape that conforms to a shape of a surface against which the extension arm 26 is intended to be anchored to. For example, the extension arm 26 can have a shape that contours the shape of a portion of a vertebra. The length $l_e$ of the extension arm 26 can also vary, but it preferably has a length $l_e$ that is sufficient to allow a fastener to be mated thereto without interference from the head 22 of the bone screw 20. The extension arm 26 can also include one or more thru-bores formed therein for receiving a fastener for anchoring the extension arm 26 to bone. As shown in FIGS. 2A and 2B, the extension arm 26 includes a thru-bore 26a formed in a terminal end thereof for receiving a fastener therethrough. In this embodiment, the thru-bore 26a is sized to receive a secondary screw 28 therethrough, as shown. However, the thru-bore 26a can receive various other fasteners, and the configuration can vary depending on the configuration of the fastener. By way of non-limiting example, FIG. 3 illustrates a bone screw 30 having an extension arm 36 with a thru-bore 36a that is smaller than the thru-bore 26a shown in FIGS. 2A and 2B. The thru-bore 36a is sized to receive a wire therethrough, rather than a secondary screw. The wire can be threaded through the thru-bore 36a and anchored to bone using various anchoring techniques known in the art.

Referring back to FIGS. 2A-2B, in use the bone screw 20 is implanted in bone at a first fixation point, and the fastener, i.e., the secondary bone screw 28, is inserted through the thru-bore 26a in the extension arm 26 and it is implanted in bone at a second fixation point located adjacent to the first fixation point. As a result, the second point of fixation will prevent rotation of the bone screw 20, thereby preventing loosening and providing a more secure fixation. As previously explained, this is particularly advantageous during unilateral fixation to counteract the offset forces. While not shown, a person skilled in the art will appreciate that the bone screw 20 can include one or more additional extension arms, and that the extension arms can extend from various locations of the bone screw 20, including various portions of the head 22 and/or the shank 24.

Figure 4A:
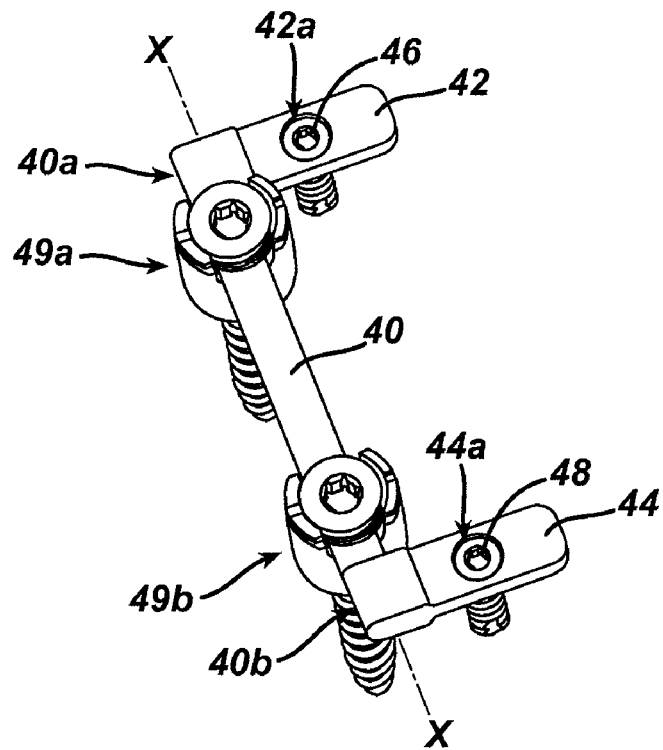
FIG. 4A is a perspective view of another embodiment of an extension member in the form of first and second extension arms extending laterally from opposed distal ends of a spinal connector and having thru-bores formed therein with secondary bone screws disposed therethrough for anchoring the extension arms to bone to prevent rotation of one or more bone anchors coupled to the spinal connector.
Figure 4B:
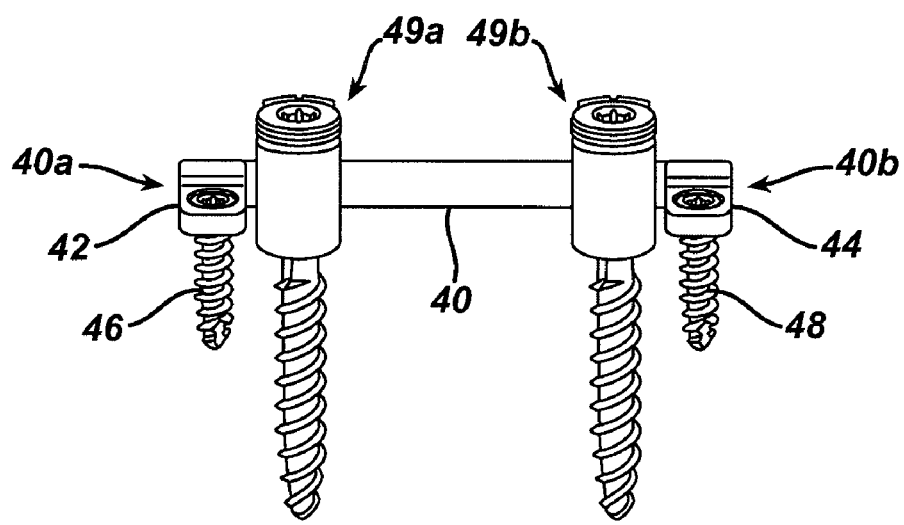
FIG. 4B is a side view of the system of FIG. 4A.

FIGS. 4A and 4B illustrate another technique for providing a second point of fixation. In this embodiment, rather than having an extension member fixedly mated to or formed on a portion of a bone anchor, the extension member is mated to or formed on a spinal connector that can be coupled to one or more bone anchors. In particular, FIGS. 4A and 4B illustrate an elongate spinal rod 40 having a first extension arm 42 extending outward from a first terminal end 40a thereof, and a second extension 44 arm extending outward from a second terminal end 40b thereof. The first and second extension arms 42, 44 can extend at various angles relative to a longitudinal axis X of the spinal rod 40, but as shown in FIGS. 4A and 4B the extension arms 42, 44 extend generally perpendicular to the longitudinal axis X of the spinal rod 40. Each extension arm 42, 44 has a generally elongate, planar configuration and includes a thru-bore 42a, 44a formed in a portion thereof for receiving a fastener, such as a secondary bone screw 46, 48 as shown. The particular location of the thru-bores 42a, 44a, as well as the length and configuration of each extension arm 42, 44, can vary depending on the intended implant site of the spinal rod 40 and the fasteners 46, 48. While not shown, the extension arms 42, 44 can also be positioned at various other locations along the spinal rod 40, and the spinal rod 40c an include any number of extension arms.

In use, the spinal rod 40 can be anchored to one or more vertebrae, preferably by mating the spinal rod 40 to one or more bone anchors implanted in one or more adjacent vertebrae such that the spinal rod extends longitudinally along a lateral side of a patient's spinal column. FIGS. 4A and 4B illustrate the spinal rod 40 coupled to first and second bone screws 49a, 49b, which can be implanted in first and second adjacent vertebrae. The bone screws 49a, 49b are similar to the bone screw 14 previously described with respect to FIG. 1B. A fastener can be implanted in each extension arm 42, 44 to anchor the extension arms 42, 44 to bone at a second fixation point. As shown in FIGS. 4A and 4B, the fasteners are in the form of secondary screws 46, 48 that are inserted through the thru-bores 42a, 44a in the first and second extension arms 42, 44 for anchoring the first and second extension arms 42, 44 to bone at a location adjacent to the bone screws 49a, 49b. In other words, the first and second fixation points for bone screws 49a and 46 are located in a first vertebra, and the first and second fixation points for bone screws 49b and 48 are located in a second adjacent vertebra. As a result, the second point of fixation on each vertebra will prevent the spinal rod 40 from moving, thereby preventing rotation of the head of the primary bone screws 49a, 49b. As previously explained, this is particularly advantageous during unilateral fixation to counteract the offset forces.

A person skilled in the art will appreciate that a variety of other fasteners can be used in place of the fasteners shown in FIGS. 1B-3. Exemplary fasteners include, by way of non-limiting example, nails, spikes, tacks, staples, wires, rivets, hooks, clamps, expandable fasteners, bolts, screws, etc. Moreover, a variety of other bone anchors, i.e., bone screws 14, 20, 30, 49a, 49b, can also be used including, for example, spinal plates, spinal hooks, etc.

Figure 5:
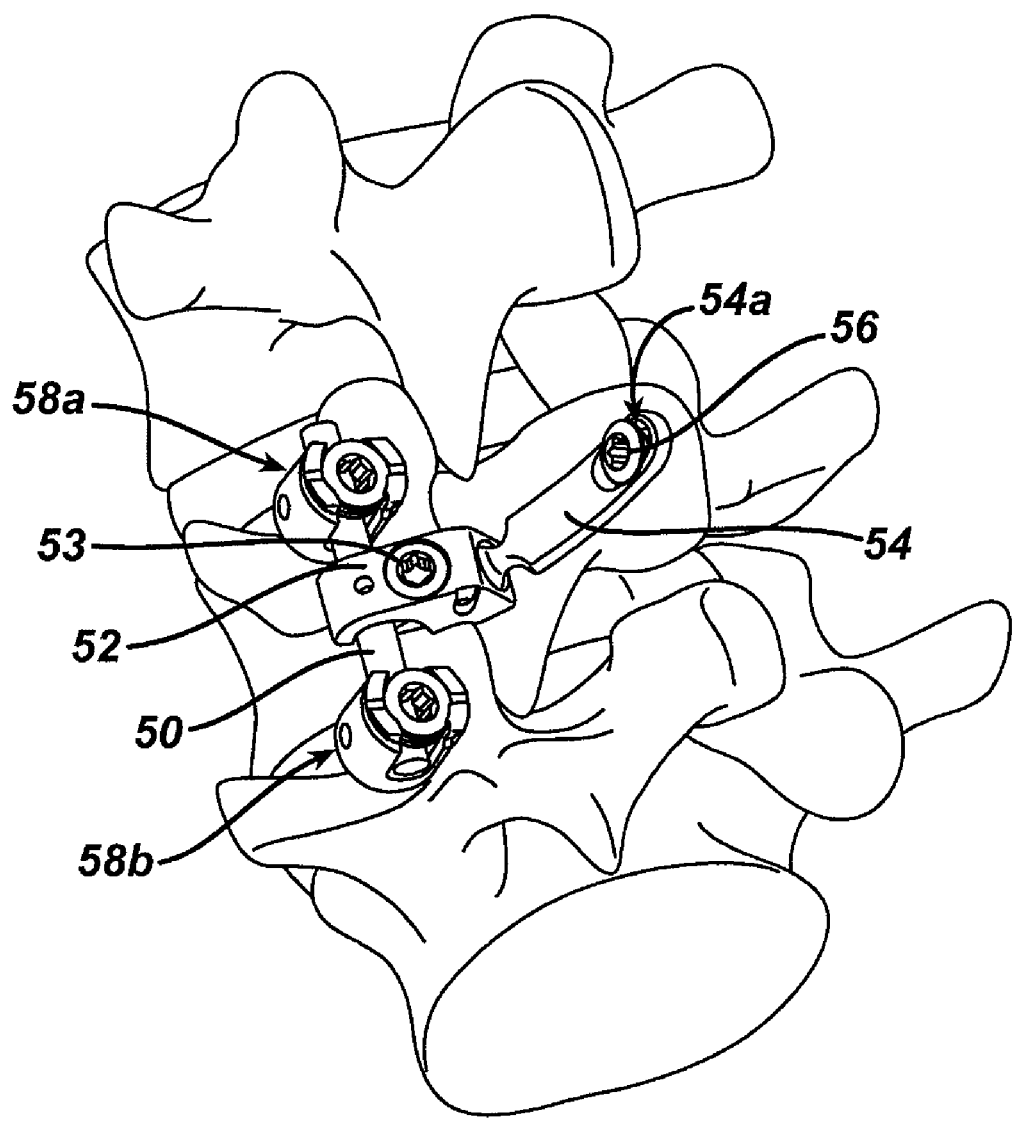
FIG. 5 is a perspective view of yet another embodiment of an extension member in the form of cross-connector removably matable to a spinal connector extending laterally along a spinal column, and an arm movably coupled to the cross-connector and having a thru-bore formed in a terminal portion thereof with a fastener disposed therethrough for anchoring the extension member to the spinous process.

FIG. 5 illustrates yet another embodiment of an extension member for providing a second point of fixation. In this embodiment, the extension member is removably mated to a spinal rod 50. In particular, the extension member includes a cross-connector 52 removably matable to the spinal rod 50, and an arm 54 coupled to the cross-connector 52 and having a thru-bore 54a formed in a terminal portion thereof for receiving a fastener for anchoring the extension member to bone. The cross-connector 52 can have a variety of configurations, but as shown in FIG. 5 it is adapted to be disposed around and to engage a spinal rod 50. The cross-connector 52 can include a locking mechanism, such as a set screw 53, for locking the cross-connector 52 onto the rod 50. The arm 54 that extends from the cross-connector 52 can be fixedly mated to or formed integrally with the cross-connector 52, or it can be pivotally coupled to the cross-connector 52. In the embodiment shown in FIG. 5, the arm 54 includes a ball (not shown) formed on a terminal end thereof that is disposed within a socket (not shown) formed in the cross-connector 52 for allowing pivotal movement of the arm 54 relative to the cross-connector 52. Such a configuration will facilitate positioning of the arm 54 relative to bone to which the arm 54 is to be anchored. As further shown in FIG. 5, the arm 54 can have a curved configuration. This is particularly useful for anchoring the arm 54 to the spinous process S of a vertebra, as shown. The arm 54 can be anchored to the vertebra using a fastener, such as a secondary bone screw 56. Once anchored, the arm 54 will help maintain the spinal rod 50 in a fixed position, thereby preventing rotation of one or more bone anchors, such as bone screws 58a, 58b, that are coupled to the rod 50 and that are implanted in adjacent vertebrae.

The present invention also provides exemplary methods for unilateral fixation. In one exemplary embodiment, a spinal fixation construct can be implanted in a patient's spine. In particular, a bone anchor, such as a bone screw, can be implanted in each vertebra to be affixed at a first fixation point on one lateral side of the spine. The opposed lateral side of each vertebra will remain un-affixed. A spinal connector, such as a spinal rod or plate, can be mated to the bone anchors implanted in the lateral side of the spine such that the spinal connector extends longitudinally along the lateral side of the spine. In order to counteract any offset forces received as a result of affixing only one lateral side of the spine, one or more of the bone anchors and/or the spinal connector can be anchored to bone at a second fixation point. For example, a fastener, such as a screw, wire, etc., can be disposed through an extension member mated to one or more of the bone anchors or to the spinal connector. In certain exemplary embodiments, the fastener is implanted in the vertebra at a location adjacent to the bone anchor, i.e., the first and second fixation points are located adjacent to one another, preferably in the same vertebra. As a result, the second fixation point will prevent rotation or other movement of the bone anchor, thereby counteracting the offset forces occurring as a result of the unilateral fixation.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A unilateral fixation device, comprising:
   a bone anchor having a head with opposed arms that define a receiving recess therebetween that is configured to seat a spinal connector, and a bone-engaging member extending distally from the head and configured to engage bone, the bone-engaging member and the head extending along a common longitudinal axis; and
   an extension member formed on and extending outward from a proximal terminal end of one of the opposed arms of the head of the bone anchor, the extension member including at least one thru-bore formed therein and configured to receive a fastener for anchoring the extension member to bone at a location adjacent to the bone anchor.

2. The device of claim 1, wherein the extension member comprises an elongate arm having a thru-bore formed in a terminal portion thereof.

3. The device of claim 1, further comprising a fastener for anchoring the extension member to bone.

4. The device of claim 3, wherein the fastener comprises a secondary bone screw.

5. The device of claim 3, wherein the fastener comprises a wire.

6. The device of claim 1, wherein the bone anchor comprises a bone screw and the bone-engaging member comprises a shank extending distally from the head and configured to engage bone.

7. A unilateral fixation system, comprising:
   a bone screw having a head having opposed arms that define a recess therebetween, and a shank extending distally from the head and configured to engage bone;
   a spinal connector configured to be received within the recess in the head; and
   at least one extension member formed on and extending laterally from a proximal terminal end of one of the opposed arms of the head, the at least one extension member including at least one thru-bore formed therein for receiving a fastener for anchoring the extension member to bone such that a longitudinal axis of the fastener is substantially parallel to a longitudinal axis of the bone screw.

8. A method for spinal fixation, comprising:
   implanting a bone anchor at a first fixation point in a lateral side of a vertebra of a spine;
   coupling a spinal connector to the bone anchor such that the spinal connector extends along the lateral side of the spine; and
   implanting a fastener in the same lateral side of the vertebra adjacent to the bone anchor, the fastener extending through an extension member extending from a proximal terminal end of the bone anchor such that a longitudinal axis of the fastener is substantially parallel to a longitudinal axis of the bone anchor, and such that the fastener provides a second point of fixation adjacent to the first point of fixation and prevents rotation of the bone anchor.

9. The method of claim 8, wherein the bone anchor comprises a bone screw.

10. The method of claim 8, wherein the second point of fixation is in the spinous process of the vertebra.

11. The method of claim 8, wherein the fastener comprises a secondary bone screw that is inserted through a thru-bore formed in the extension member.

12. The method of claim 8, wherein the fastener comprises a wire that is threaded through a thru-bore formed in the extension member.

13. The method of claim 8, further comprising implanting a plurality of bone anchors in a lateral side of a plurality of adjacent vertebrae, and mating the spinal connector to the plurality of bone anchors to unilaterally affix the adjacent vertebrae to one another.

14. The method of claim 8, wherein the bone anchor includes a head having opposed arms that seat the spinal connector, and the extension member is directly fixed to one of the opposed arms of the head to prevent rotation of the bone anchor when the fastener is implanted through the extension member.

\* \* \* \* \*

UNITED STATES PATENT AND TRADEMARK OFFICE
CERTIFICATE OF CORRECTION

| | | |
|---|---|---|
| PATENT NO. | : 7,892,260 B2 | Page 1 of 1 |
| APPLICATION NO. | : 11/539295 | |
| DATED | : February 22, 2011 | |
| INVENTOR(S) | : Mahoney et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 640 days.

Signed and Sealed this
Ninth Day of August, 2011

David J. Kappos
*Director of the United States Patent and Trademark Office*